(12) United States Patent
Anderson et al.

(10) Patent No.: US 8,147,395 B2
(45) Date of Patent: Apr. 3, 2012

(54) BONE-ACTIVITY STIMULATION APPARATUS AND METHOD

(75) Inventors: Gregory S. Anderson, Sandy, UT (US);
Pita Witehira, Hamilton (NZ);
Elizabeth P. Witehira, Hamilton (NZ);
Evan L. Bydder, Hamilton (NZ)

(73) Assignee: Gregory S. Anderson, Salt Lake City, UT (US)

( * ) Notice: Subject to any disclaimer, the term of this patent is extended or adjusted under 35 U.S.C. 154(b) by 1130 days.

(21) Appl. No.: 11/946,042

(22) Filed: Nov. 27, 2007

(65) Prior Publication Data
US 2008/0125618 A1    May 29, 2008

Related U.S. Application Data

(60) Provisional application No. 60/867,424, filed on Nov. 28, 2006.

(51) Int. Cl.
*A61N 2/00*     (2006.01)
(52) U.S. Cl. .............................. 600/14; 600/9
(58) Field of Classification Search ............ 600/9, 14
See application file for complete search history.

(56) References Cited

U.S. PATENT DOCUMENTS

| | | | |
|---|---|---|---|
| 4,105,017 A | 8/1978 | Ryaby et al. | |
| 4,266,533 A | 5/1981 | Ryaby et al. | |
| 4,315,503 A | 2/1982 | Ryaby et al. | |
| 5,014,699 A | 5/1991 | Pollack et al. | |
| 5,058,582 A | 10/1991 | Thaler | |
| 5,087,336 A | 2/1992 | Liboff et al. | |
| 5,160,591 A | 11/1992 | Liboff et al. | |
| 5,181,902 A | 1/1993 | Erickson et al. | |
| 5,269,745 A | 12/1993 | Liboff et al. | |
| 5,269,747 A | 12/1993 | Erickson et al. | |
| 5,290,409 A | 3/1994 | Liboff et al. | |
| 5,314,400 A * | 5/1994 | Tsyb et al. | 600/9 |
| 5,338,286 A | 8/1994 | Abbott et al. | |
| 5,458,558 A | 10/1995 | Liboff et al. | |
| 5,554,835 A * | 9/1996 | Newham | 200/85 R |
| 5,654,694 A | 8/1997 | Newham | |
| 5,743,844 A | 4/1998 | Tepper et al. | |
| 5,792,209 A | 8/1998 | Varner | |
| 5,951,459 A | 9/1999 | Blackwell | |
| 5,997,464 A | 12/1999 | Blackwell | |
| 6,024,691 A | 2/2000 | Tepper et al. | |

(Continued)

OTHER PUBLICATIONS

Advanced Biomagentics® Clinical Database: Osteoporosis Studies, therion®, http://www.therionresearch.com/database/osteoporosis.html#2, Nov. 11, 2006.

(Continued)

*Primary Examiner* — Charles A Marmor, II
*Assistant Examiner* — Joshua D Lannu
(74) *Attorney, Agent, or Firm* — Pate Baird, PLLC

(57) ABSTRACT

A method of increasing bone mass throughout the body of a user. The method may include the steps of obtaining a distributor comprising a plurality of electromagnetic coils, obtaining a controller comprising a processor and a memory device, operably connected to one another, the memory device storing code executable by the processor, selecting a source of electrical current, connecting the source to the controller, and positioning a user proximate the distributor. The method may further include controlling, by the controller in accordance with the code, delivery of electrical current sequentially and exclusively to each coil of the plurality of electromagnetic coils to generate a magnetic field extending into the user.

14 Claims, 8 Drawing Sheets

U.S. PATENT DOCUMENTS

| | | | |
|---|---|---|---|
| 6,132,362 | A | 10/2000 | Tepper et al. |
| 6,174,276 | B1 | 1/2001 | Blackwell |
| 6,179,772 | B1 | 1/2001 | Blackwell |
| 6,186,941 | B1 | 2/2001 | Blackwell |
| 6,200,259 | B1 | 3/2001 | March |
| 6,213,934 | B1 | 4/2001 | Bianco et al. |
| 6,261,221 | B1 | 7/2001 | Tepper et al. |
| 6,364,824 | B1 | 4/2002 | Fitzsimmons |
| 6,395,799 | B1 | 5/2002 | Johnson |
| 6,418,345 | B1 | 7/2002 | Tepper et al. |
| 6,443,883 | B1 | 9/2002 | Ostrow et al. |
| 6,463,336 | B1 | 10/2002 | Mawhinney |
| 6,560,487 | B1 | 5/2003 | McGraw et al. |
| 6,561,968 | B1 | 5/2003 | Dissing et al. |
| 6,675,048 | B2 | 1/2004 | McGraw et al. |
| 6,792,315 | B2 | 9/2004 | Carter et al. |
| 6,819,210 | B2 | 11/2004 | Boynton et al. |
| 6,839,595 | B2 * | 1/2005 | Tepper et al. ................... 607/51 |
| 6,853,863 | B2 | 2/2005 | Carter et al. |
| 6,853,864 | B2 | 2/2005 | Litovitz |
| 6,856,839 | B2 | 2/2005 | Litovitz |
| 6,955,642 | B1 | 10/2005 | Simon |
| 7,010,353 | B2 | 3/2006 | Gan et al. |
| 7,130,692 | B2 | 10/2006 | Brighton et al. |
| 7,158,835 | B2 | 1/2007 | Brighton et al. |
| 7,175,587 | B2 | 2/2007 | Gordon et al. |
| 2002/0151760 | A1 * | 10/2002 | Paturu ............................. 600/15 |
| 2002/0165583 | A1 | 11/2002 | Tepper et al. |
| 2003/0095022 | A1 | 5/2003 | Boynton et al. |
| 2003/0158585 | A1 | 8/2003 | Burnett |
| 2004/0210254 | A1 | 10/2004 | Burnett |
| 2005/0124846 | A1 * | 6/2005 | Pasula et al. ....................... 600/9 |
| 2005/0182287 | A1 | 8/2005 | Becker |
| 2005/0267355 | A1 | 12/2005 | Parker |
| 2006/0212077 | A1 | 9/2006 | Pilla et al. |

OTHER PUBLICATIONS

*An Electrical Device to Make Bones Grow*, http://www.thirdage.com/ebsco/files/14707.html, Oct. 21, 2007.

http://www.scielo.br/scielo.php?pid=S0100-879X2006005000030&script=sci_arttext.

*Pulsed Electromagnetic Fields for Bone Health and Bone Healing*, QRS World of Health, http://www.qrsworldofhealth.com/osteoporosis_intro.html, Oct. 9, 2007.

Hiromasa Miura, *Application of a Pulsed Electromagnetic Field for the Treatment of Osteoporosis*, Department of Orthopaedic Surgery, Kyushu University.

Kyle Chang, Walter Hong-Shong Chang, Yen-Hsin Yu, Chung Shih, *Pulsed Eectromagnetic Field Stimulation of Bone Marrow Cells Derived from Ovariectomized Rats Affects Osteoclast Formation and Local Factor Production*, May 14, 2003, (Abstract Only), http://www3.interscience.wiley.com/search/allsearch?mode=viewselected&product=journal&ID=107061128&view_selected.x=69&view_selected.y=9.

Jitendra Behari and Jayanand, *Low Level Pulsed Radio Frequency Field and Its Remedial Effect on Osteoporosis and Bone Fracture*, Progress in Electromagnetics Research Symposium 2005, Aug. 22-26, 2005, pp. 736-739 Hangzhou, China.

Lirani-Galvãão, C.T. Bergamaschi, O.L. Silva and M. Lazaretti-Castro, Electrical Field Stimulation Improves Bone Mineral Density in Ovariectomized Rats, Brazilian Journal of Medical and Biological Research, Nov. 2006, 1501-1505; http://www.scielo.br/pdf/bjmbr/v39n11/6295.pdf.

* cited by examiner

BONE-ACTIVITY STIMULATION APPARATUS AND METHOD

RELATED APPLICATIONS

This application claims the benefit of U.S. Provisional Patent Application Ser. No. 60/867,424 filed Nov. 28, 2006, which is incorporated by reference herein.

BACKGROUND

1. The Field of the Invention

This invention relates to electromagnetic simulation of bone stress, and more particularly to methods and apparatus to stimulate or otherwise induce electrical activity in bones of a subject in order to elicit a positive response such as natural generation of increased bone density.

2. The Background Art

Human tissues are electrical apparatus. Likewise animal tissues are electrical apparatus. A complex assembly of structure, chemistry, and electrical connection controls and implements the activity, growth, healing, and other functions of living tissues of the animal kingdom. Manipulating the structures of tissues, whether soft tissue or bone tissue has been purview of the surgical portion of the medical community. Manipulation of chemistry has been the purview the drug portion of the medical community. Manipulation of the electrical activities of body tissues has largely been left to the other two fields, surgical and chemical treatments.

There has been a development of an electrical treatment community in the medical field, particularly, dealing with electro-stimulation. However, many researchers in the field often claim a lack of understanding of the specific phenomena that affect the correlation between electrical stimulation and organic functioning of live animal tissues. Nevertheless, electrical stimulation therapy has been used in both invasive and noninvasive systems for directly applying electrical potential to stimulate a response.

Within the medical community, selected, time-varying electric and magnetic fields have played an increasingly successful role in the care of several challenging medical problems, mainly fractures that have failed to heal, in both children and adults, as well as chronic skin wounds. This progress has been made over the past decades.

Bioelectromagnetics is a term applied to a field developing in the biological sciences and devoted to the interaction between living organisms and electromagnetic fields. Electrical phenomenon are inherent in most living organisms, and certainly in all animal organisms. For example bones, nerves, cartilage, muscle, and the like have been considered to contain electrical connections and circuits for their normal operation. Accordingly, these electrical circuits can be influenced by external magnetic fields and electromagnetic fields. Publications indicate that electromagnetic fields operating at frequencies below 300 hertz can influence biological functions. Some controversy exists regarding the mechanics of operation of these interactions.

Pulsed electromagnetic fields in medicine are not new. Static magnets and electrical current have been used for years. In modern medicine however, it was in about the 1970's that the United States FDA approved a pulsed electromagnetic field device to assist in the healing of non-union fractures. Doctor C.A.L. Basset pioneered work leading to an 80% success rate in the healing of non-union fractures without any side effects. Accordingly, therapy by pulsed electromagnetic fields is recognized as effective in bone healing in the medical profession.

Meanwhile, additional detailed work has been done on a cellular level in vitro and in vivo to evaluate the efficacy of pulsed electromagnetic fields on bone density. Much of the work seems to be devoted to establishing a specific biological mechanisms by which electromagnetic fields couple to body chemistry and cellular activity.

With the magnetic fields induced by an MRI machine, molecular dipoles orient along the magnetic field lines. Once the magnetic field is collapsed, the dipoles, actual physical molecules, rotate back to their original positions. The return to the original positions generates another magnetic pulse, which pulse is detected and used to reconstruct in a computer an image of the tissues within the MRI field.

Thus, electromagnetic fields are not only known to affect body tissues, but body tissues themselves generate magnetic fields by their own motion, which magnetic fields are sufficiently strong to be detected and analyzed by sophisticated signal processing in order to image tissues and boundaries of tissues in the body.

Likewise, the bone structures of a body are known to have a piezoelectric characteristic. That is, they respond to stress by creating an electrical potential. Likewise, however, since piezoelectric events are symmetric. The application of electrical potential will then cause stress.

What is needed is a system implementing a method and apparatus for coupling, non-invasively, an external electromagnetic field to the body tissues that may provide electrical stimulation to bones.

It would be an advance in the art to improve non-invasive electro-stimulation by magnetic coupling of an electrical system outside of a subject with the electrical system within a subject.

BRIEF SUMMARY OF THE INVENTION

In view of the foregoing, in accordance with the invention as embodied and broadly described herein, a method and apparatus are disclosed in one embodiment of the present invention as including a distributor comprising a plurality of electromagnetic coils. A controller may control the operation of the distributor. The controller may include a processor and a memory device operably connected to one another, the memory device storing code executable by the processor. The controller may be connected to a source of electrical current. During operation, a user may be positioned proximate the distributor (e.g., recline or lie over or below the distributor). The controller may then control, according to the code, delivery of electrical current to the coils. In one embodiment, the controller may deliver current sequentially and exclusively to each coil to generate a magnetic field extending into the user.

In accordance with the foregoing, an apparatus and method in accordance with the invention implement a magnetic coil providing a magnetic field penetrating a depth into a body sufficient to provide the designated field strength near a bone thereof. Accordingly, in an apparatus and method in accordance with the invention, the magnetic field acts in several ways.

First, as the field is established, and as it collapses, it is effectively capable of inducing currents in circuits within the field. That is, whenever a circuit moves through a magnetic field, or a magnetic field moves across a circuit current is induced in the circuit. Thus, electrical circuits within the magnetic field generated by an apparatus will obey the law of physics and generate currents. Whether a circuit is formed of wire or of animal tissues, relative motion between the circuit and the magnetic field will generate electrical currents in the circuit.

Second, by generating a magnetic field, certain molecular dipoles in cells within the body will undergo alignment or a tendency to align with the field lines of the applied magnetic field. This provides an actual mechanical displacement stimulation.

Third, any generation of an electrical potential across a piezoelectric element causes stress and typically strains at a "micro" level. This stress and strain is not distinguishable from "macro" level stresses and strains corresponding to exercise.

Applicants observed in the use of electromagnetic stimulation for bone healing of fractures in persons having poor bone repair function (e.g., smokers, diabetics, poor circulation subjects, etc.) that electromagnetic stimulation aided both fracture healing and joinder of fused constituents. However, following treatments effective to aid the bone healing, it was observed that even on the gross scale provided by X-ray images, an increase in bone density was apparent. Thus, Applicants engineered a system to augment bone density increase over the entire body. Applying a local electromagnetic field to one location of the body is not scalable by simply adding more devices, to treat the entire body with a mechanism of electromagnetic therapy.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 10 illustrates one example of an embodiment of a distributor of an apparatus in accordance with the invention, illustrating one implementation for a double bed cover, blanket, mattress-cover, or the like.

DETAILED DESCRIPTION OF THE INVENTION

Figure 1:
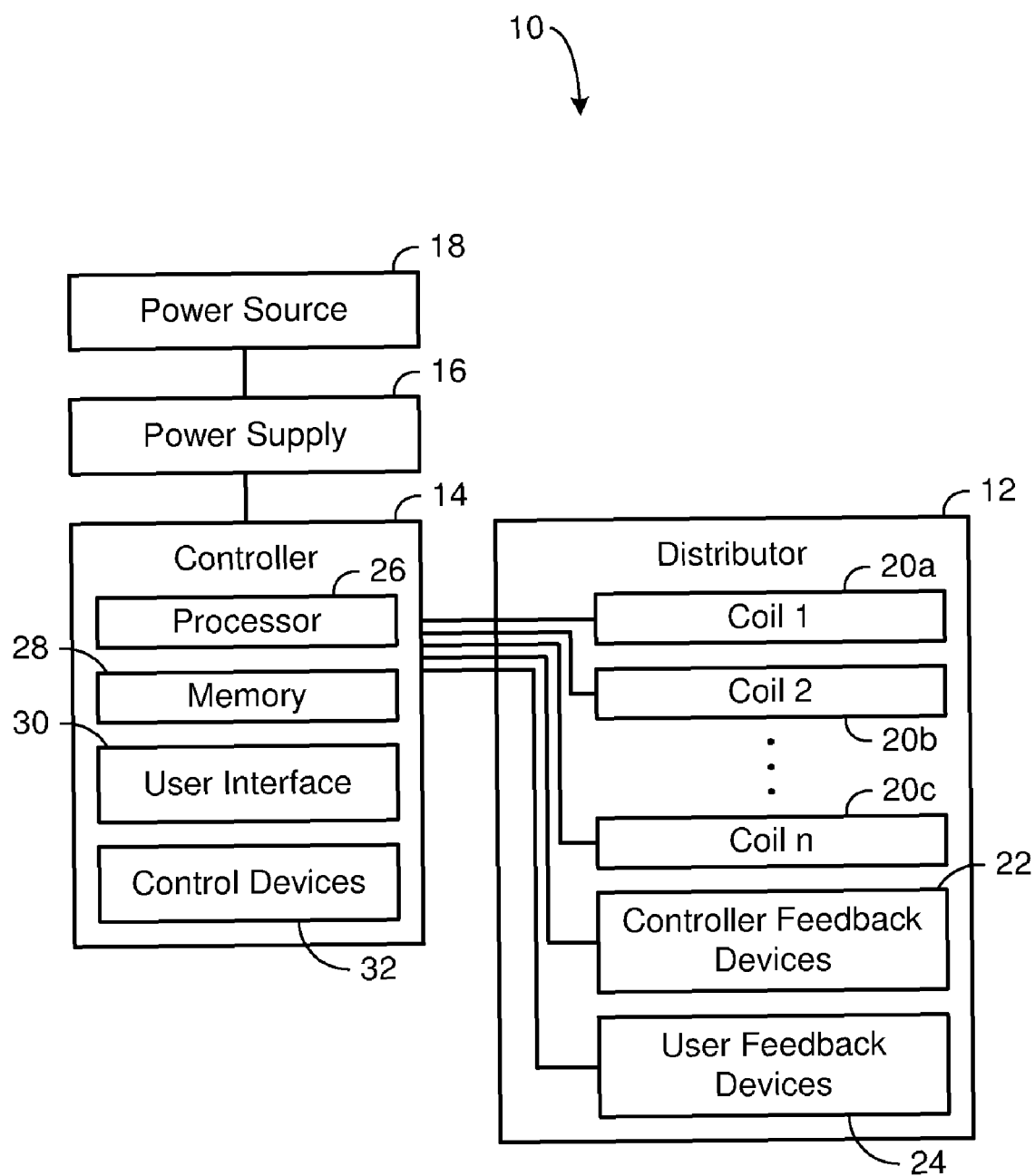
FIG. 1 is a schematic diagram of an apparatus in accordance with the invention.

It will be readily understood that the components of the present invention, as generally described and illustrated in the drawings herein, could be arranged and designed in a wide variety of different configurations. Thus, the following more detailed description of the embodiments of the system and methods of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, an apparatus 10 in accordance with the invention may include a distributor 12 effective to distribute electromagnetic flux through a subject or user. The distributor 12 may be controlled by a controller 14. The controller 14 may control current, duration, frequency, and the like for the electromagnetic flux provided by the distributor 12 to a subject.

A power supply 16 may provide conditioned power to the controller 14. The power supply 16 may be adapted to receive electric power from a power source 18 such as conventional wall current, multi-phase current available on distribution in a building, a generator, or the like. In selected embodiments, a power supply 16 may convert alternating current (AC) received from the power source 18 into low voltage DC power suitable for operating the controller 14. A power supply 16 may also condition power to be provided to the distributor 12.

In certain embodiments, a distributor 12 may include multiple coils 20a, 20b, 20c, each formed of several turns of an electrical conductor. When energized with current, each coil 20 may become an electromagnetic coil creating an electromagnetic field. A distributor 12 in accordance with the present invention may also include one or more feedback devices 22.

A feedback device 22 may provide information assisting the controller 14 in controlling the distributor 12. For example, various types of feedback devices 22 may be implemented including human actuated controls, detectors for detecting the presence of a user, temperature sensors, current sensors, or the like. In selected embodiments, the feedback devices 22 may insure safety, proper operation, limit duty cycles, and so forth.

In addition to controller feedback devices 22, a distributor 12 may include user feedback devices 24. A user feedback device 24 may provide confirmation to the user that the apparatus or distributor 10 is functioning properly. That is, a user without additional aids may be unable to perceive the electromagnetic field or fields being generated by a system 10 in accordance with the present invention. Accordingly, a system 10 may include one or more feedback devices 24 providing visual confirmation of activity. Such devices 24 may include light-emitting diodes (LEDs), displays, lights, or the like to encourage or sustain a user in his or her use of the system 10.

In selected embodiments, a controller 14 may include a processor 26 operably connected to a memory device 28. A memory device 28 may store the applications, programs, or code executed by the processor 26 during operation of the system 10. In selected embodiments, a processor 26 and memory device 28 may collectively be embodied as a microprocessor.

In certain embodiments, a controller 14 may include a user interface 30 receiving inputs from a user. For example, certain interfaces 30 may include keypads, switches, knobs, buttons, touch screens, monitors, or other mechanisms for interaction with a user in generating electrical signals to be received by a processor 26. Accordingly, a user may enter program parameters, timing information, duration information, frequency control information, current information, or the like and thereby influence or control operation of the distributor 12.

Likewise, a user may select a particular intensity of electromagnetic field, frequency thereof, or the like. Alternatively, certain parameters may be "hardwired" into a controller 14 while others may be controlled through a user interface 30.

In selected embodiments, a user interface 30 may accept inputs that are more qualitative then quantitative to a user. Such inputs may be translated by a processor 26 into specific engineering and physics terms or variables suitable for implementation. For example, a user may input selection of a long or short session. A user may input a request for a weak, medium, or strong intensity, and the like. Accordingly, preselected ranges may be programmed into the processor 26 in order to comply with the user's qualitative requirements with quantitative data that will be used by the processor 26 when controlling the distributor 12.

A user interface 30 in accordance with the present invention may also provide selected feedback or information to a user. For example, a user interface 30 may include one or more displays. In certain embodiments, the operating conditions of a controller 14 may show in a display. The display may show simultaneously, sequentially (e.g., cycle through), or as instructed by a user any or all parameters. Parameters may include repetition frequency, pulse current, duty cycle, magnetic field values, or other parameters of the system 10. A display may also show treatment progress, time elapsed, time to end of treatment, or the like, and may include audio or other outputs to signal various stages of the session (e.g., the end of the session).

In selected embodiments, a controller 14 may include one or more control devices 32. A control device 32 may implement the control functions specified by the processor 26 of the controller 14. For example, a control device 32 may include control circuitry (e.g., logic, switches, various relays, etc.) translating a control signal from the processor 26 into an actual current delivered to a specific coil 20 of the distributor 12.

A controller 14, through a processor 26, may dictate the current waveforms supplied to the coils 20 of a distributor 12. Parameters dictated by a controller 14 may include pulse repetition frequency, pulse amplitude, duty cycle of pulse current, duration of treatment sessions, or the like. Such parameters may be fixed at the time of manufacture or be selectable by a user or treatment controller (e.g., medical personnel).

Figure 2:
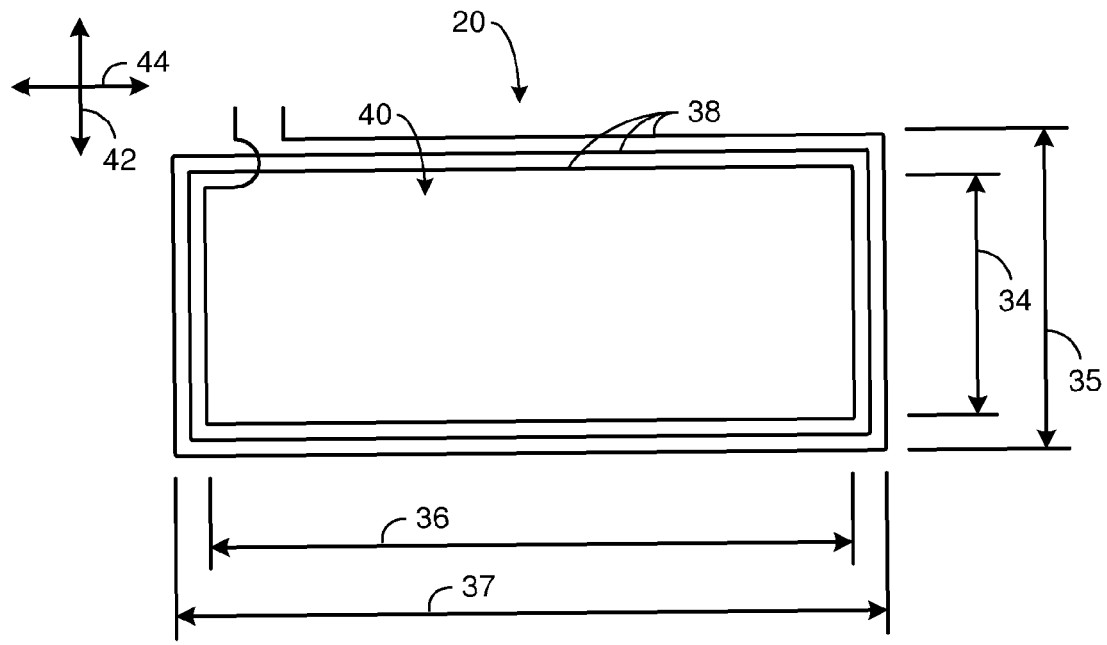
FIG. 2 is a schematic top plan view of a coil in the apparatus of FIG. 1.
Figure 3:
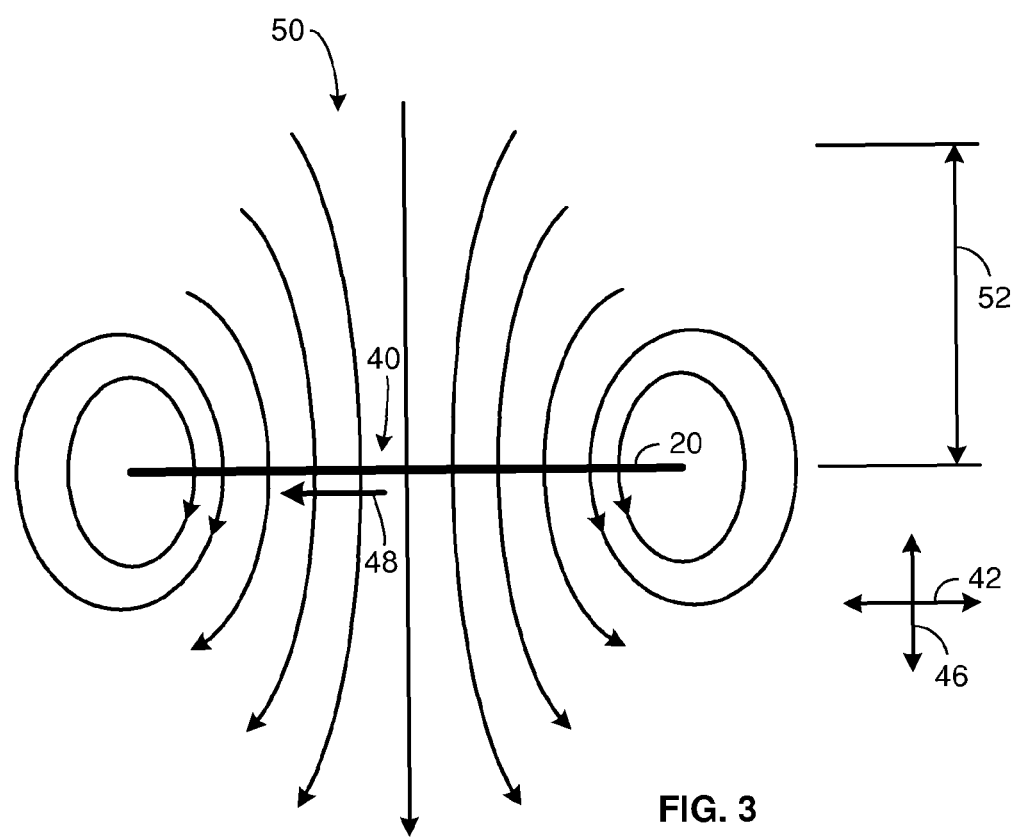
FIG. 3 is an end view of the coil of FIG. 2.

Referring to FIGS. 2-3, an apparatus 10 in accordance with the invention may include several coils 20 each having a specified interior width 34 as well as an exterior width 35. Typically, it is good magnetic design to maintain the interior width 34 as close to the exterior width 35 as possible. Nevertheless, to be more comfortable for a user, it may be preferable to distribute wires or cables further apart in order to avoid a sensation or feel of too much weight or stiffness in a particular area of the distributor 12.

Likewise, the coils 20 may each have an interior length 36 as well as an exterior length 37. The interior width 34 and interior length 36 may establish a flux window through which the magnetic flux of the coil 20 passes. The dimensions 34, 35, 36, 37 of the coil 20, as well as the number of turns 38 of the coil 20, may be used to control the magnetic strength of flux generated by the coil 20. The current passing through the turns 38 of the coil 20 may also provide a degree of control over the magnetic flux.

Accordingly, a window 40 or aperture 40 may represent the area filled with the flux of the magnetic field generated by current through the turns 38 of the coil 20. In general, the coil 20 will extend in a longitudinal direction 42 and the lateral direction 44, corresponding, typically, to the width 34 and the length 36, respectively. Thus the flux through the aperture 40 or window 40 passes in the transverse direction 46 through the window 40.

As can be determined by the directional arrows 42, 44, 46, the illustration of FIG. 3 represents an end view of the coil 20 of FIG. 2. Thus, the direction of current flowing through the coil 20 or through the turns 38 of the coil 20 is illustrated by the arrow 48. The direction 48 of current controls, according to the respective laws of physics, the direction of the magnetic field 50 passing through the window 40.

Meanwhile, the depth 52 of the magnetic field 50 may characterize the strength of a field 50 at a certain distance from the coil 20. That is, for example, the earth has a magnetic field that extends from pole to pole and extends out through a large volume of space. Similarly, the coil 20 has the ability to create flux lines 50 that extend far away. Nevertheless, at greater distances 52, the intensity or strength of the flux 50 may be less.

For example, near the actual wires forming the turns 38 of the coil 20, a very tightly turned flux 50 may be generated. Meanwhile, near the center of the coil 20, the flux lines may be substantially perpendicular or "normal" to the plane of the coil 20. While lines of flux 50 near the turns 38 themselves may close in a comparatively "tight" loop, the lines of flux 50 nearer to the center may extend a far distance before they eventually turn back and enclose on themselves in a loop. Necessarily, the flux density out in that large expanse of space may be commensurately small.

By contrast, the flux density within the window 40 containing the same amount of flux will be comparatively higher. Thus, the width 34 and length 36 of a coil 20 may create a flux distribution of a desired intensity within the window 40 and a desired intensity at a distance 52 corresponding to the depth of a human body.

Figure 4:
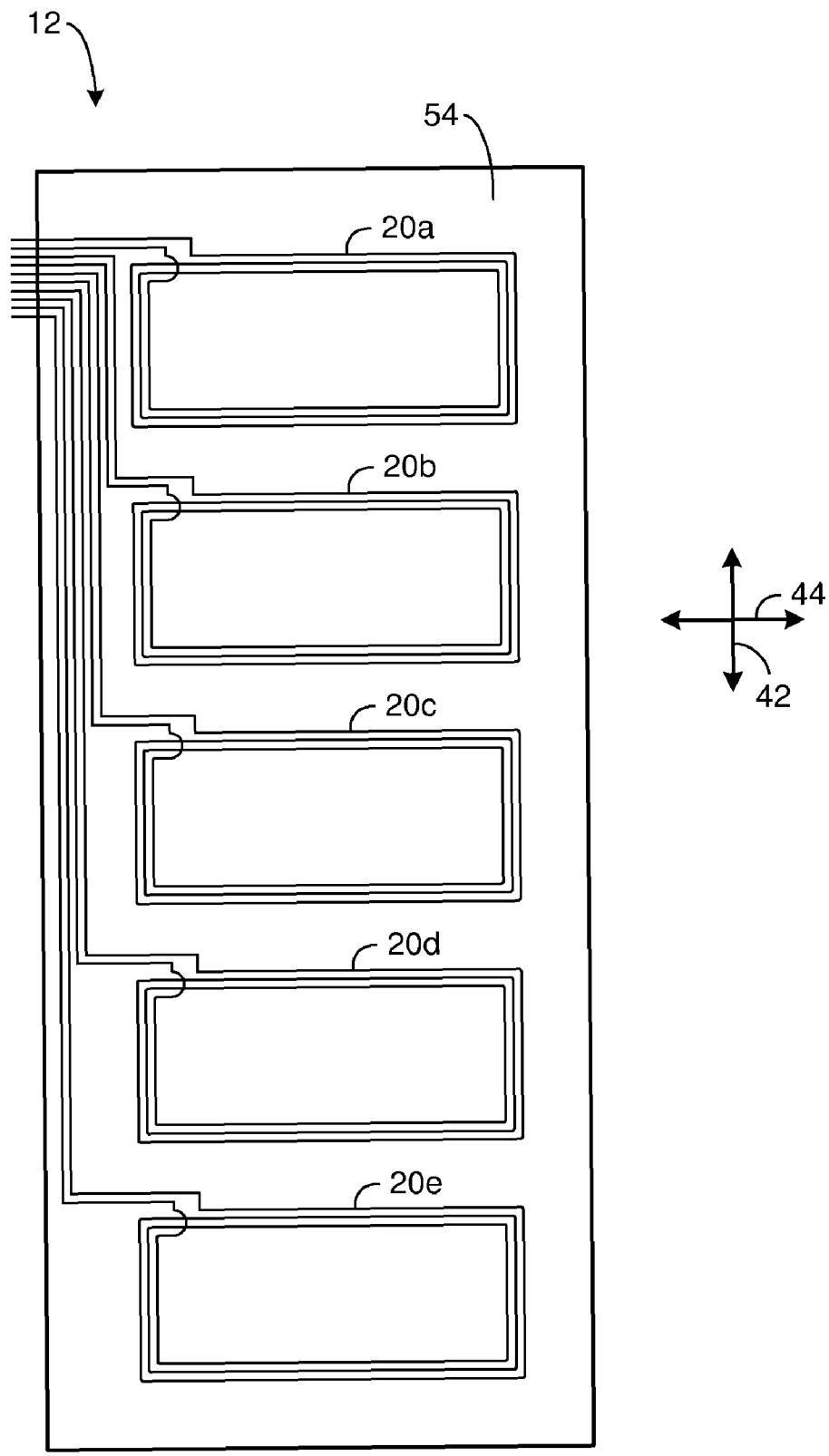
FIG. 4 is a plan view of one embodiment of the distributor portion of the apparatus of FIG. 1.

Referring to FIG. 4, in certain embodiments, when treatment is commenced, repetitive current pulses may be transferred (e.g., through cabling) to a distributor 12. A distributor 12 may include one or more coils 20, typically one to six. The coils 20 may cover a significant portion of the distributor. For example, in selected embodiments, coils 20 may consume about 60% to about 90% of the surface area of the distributor 12.

In certain embodiments, the coils 20 may be connected in series. When so connected, the overall effect is that the pulse current circulates unidirectionally around the periphery of the array of coils 20. This ensures that a patient or user will experience at least a minimum value of the electromagnetic field, typically about 25% to about 30% of the maximum field produced in the middle of the user's body. Alternatively, coils 20 may be divided into sets of one or more, with each set being sequentially pulsed. This may avoid the partial field cancellation that may otherwise occur when coils 20 (or the electromagnetic fields produced by the coils 20) overlap.

In selected embodiments, each cycle of the current waveform may include an equal number of current pulses in each directions. This may permit a distributor 12 to be positioned easily, without any preferred or required orientation. Additionally, if any area of the body is more responsive to an electromagnetic field in one direction more than in the other, that area will receive adequate stimulation.

In one embodiment of an apparatus 10 in accordance with the invention, a distributor 12 may be formed as an article of bedding. For example, a distributor 12 may comprise a matrix 54 of fabric or similar materials suitable for use as a blanket, mattress cover, layer within a mattress, or the like. The matrix 54 may provide a soft feel, warmth, or other sensory and tactile features desired by a user.

In selected embodiments, a matrix 54 may connect, stabilize, and secure the various coils 20a, 20b, 20c, 20d, 20e. Since electromagnetic flux 50 can directly interfere with and cancel other electromagnetic flux, two conditions may be maintained with respect to the coils 20. First, the coils 20 may be set in a non-overlapping arrangement in space. For example, the coils 20 may be positioned so as to be substantially coplanar (e.g., distributed in a longitudinal direction 42 along the matrix 54). Second, the coils 20 may be activated in a non-overlapping arrangement in time. That is, in selected embodiments, the controller 14 may ensure that no coil 20 is building, sustaining, or collapsing an electromagnetic field 50 at the same time that another coil 20 is building, sustaining, or collapsing an electromagnetic field 50. Thus, there is no interference between the coils 20 and no negation of the effectiveness thereof.

As a practical matter, the sequencing of energy delivery or current delivery to each of the coils 20a, 20b, 20c, 20d, 20e may be in any suitable sequence. For example, a strict sequential alternating between coils or from one coil to the next, adjacent coil may be appropriate. Likewise, a completely random distribution or sequencing between coils 20 may be acceptable and provided by the controller 14.

Moreover, since the strength of an electromagnetic field 50 may be dependent upon the electrical current and the number of turns 38 in a coil 20, electrical heating may occur if the duty cycle for a coil 20 is too high. It has been found that a duty cycle in the range of from about 2% to about 10% is adequate. With variations in current, the duty cycle may be manipulated. That is, for example, with a lower current the same magnetic flux may be obtained with more turns 38 in a coil 20. Thus, the dynamic flux 50 desired through the aperture 40 of a coil 20 may be designed to control the heat losses and the appropriate duty cycle for the apparatus 10, and for the individual coils 20.

Figure 5:
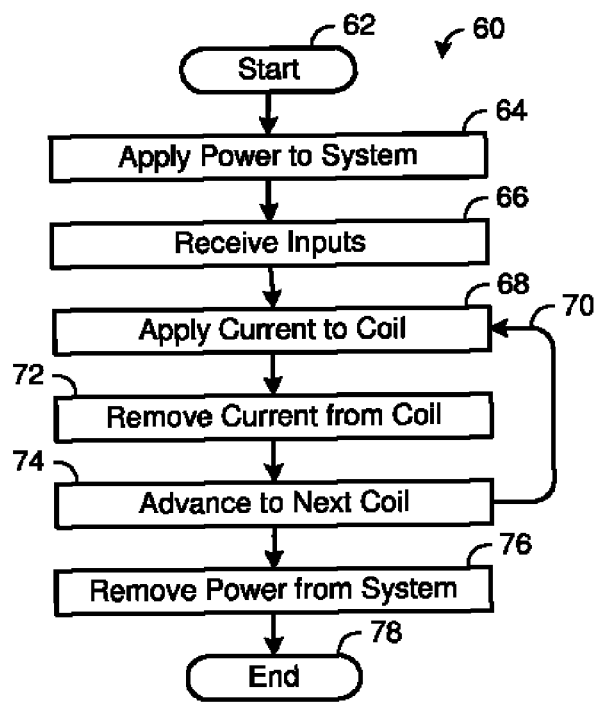
FIG. 5 is a schematic block diagram of one embodiment of a method in accordance with the invention in a very simplified form.
Figure 6:
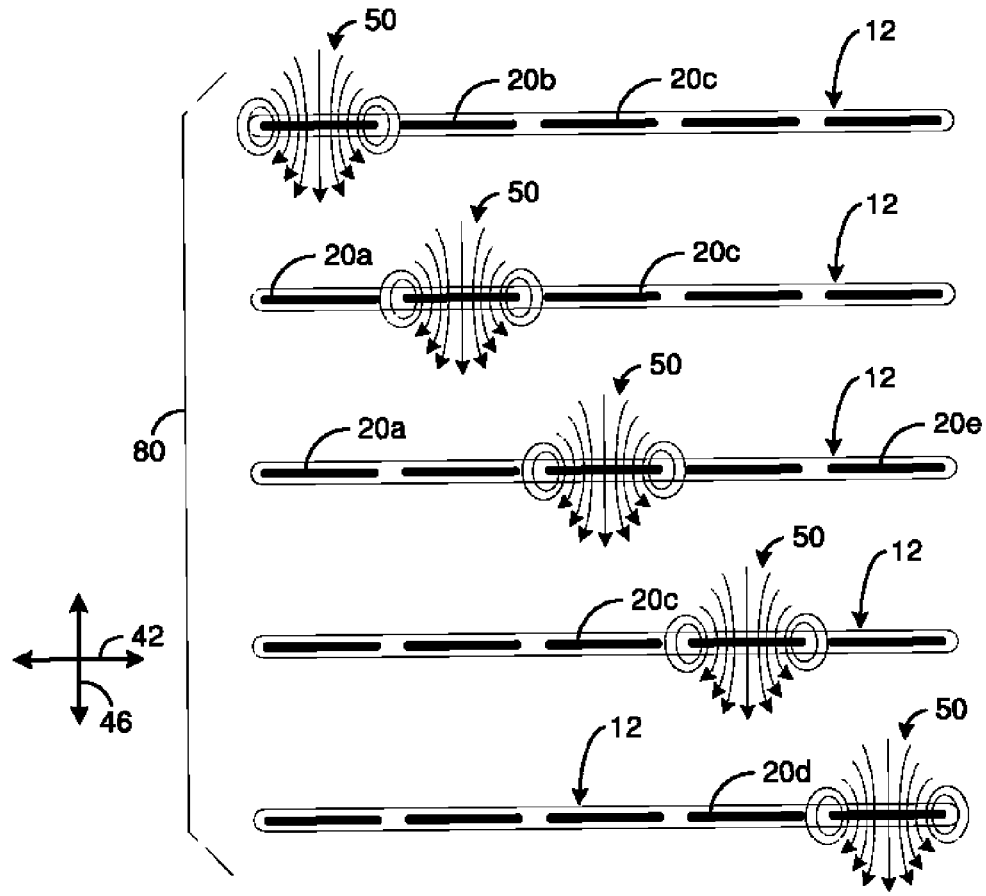
FIG. 6 is a diagram of a side elevation view of the distributor of FIG. 4 illustrating application of current and thus magnetic field as applied to each coil in sequence in accordance with the invention.

Referring to FIGS. 5 and 6, one approach to sequencing the current through the individual coils 20 may be to rely on a process 60 dictated by the controller 14. For example, upon starting 62, the process 60 may apply 64 power to the system 10. Thereafter, inputs may be received 66 by the system 10. Such inputs may include any parameters used by the processor 26 in controlling operation of the coils 20 (e.g., times, durations, intensities, frequencies, currents, or other similar values on a quantitative, qualitative, or comparable basis).

In accordance with the input received 66 or other pre-set instructions or code, the controller 14 may apply 68 current to a particular coil 20. After a preselected time, or a calculated time based on other parameters such a flux density, current, and time, or the like, the controller 14 may dictate removal 72 (termination) of the current from the coil 20.

Next, the controller 14 may advance 74 to the next coil 20 in the sequence. The controller 14 may then return 70 to application 68 of current to a coil 20, followed by a removal 72 of the current and advancing 74 to the next coil 20. The cycle of applying current 68, removing 72 current, and then advancing 74 to the next coil 20 may continue for some period of time (e.g., a session duration), in accordance with an appropriate duty cycle.

A duty cycle that is too great for a power supply 16 or for a coil 20 may cause failure of the power supply 16 or overheating of the coils 20. Accordingly, power may be removed 76 from the system 10 between activation of individual coils 20 for some extended period of time in order to enforce a duty cycle. Alternatively, power may be removed 76 from the system after cycling through all the coils 20 within the distributor 12. In yet another alternative embodiment, power may be removed 76 from the system 10 after a preselected or sensed number of cycles of applying 68 and removing 72 current from the coils 20.

The end 78 of a treatment session may be controlled by time, or by a net effective dosage of electromagnetic fields 50. For example, a user may have an exposure to higher field strength of flux 50 for a lower time or have an exposure to a lower strength of flux 50 for a greater amount of time. In certain embodiments, the field 50 or the flux density 50 and field strength may not be changeable by user, and the time may be fixed at some appropriate amount of time (e.g., one to three hours). In other embodiments, these parameters may all be changed and exchanged in order to approach the therapy desired.

Referring to FIG. 6, a sequence 80 illustrates the generation of magnetic flux 50 consequent to applying current 68 to each coil 20 in sequence. Accordingly, during a first time period, an electromagnetic field 50 may be generated from one coil 20a. In a subsequent time period, an electromagnetic field 50 may be generated from another coil 20b. In yet other subsequent time periods, electromagnetic fields 50 may be generated sequentially or in turn from the remaining coils 20c, 20d, and 20e. Thus, FIG. 6 illustrates the application 68 of current to a coil 20, followed by removal 72 thereof and advancing 74 to the next loop 20.

Figure 7:
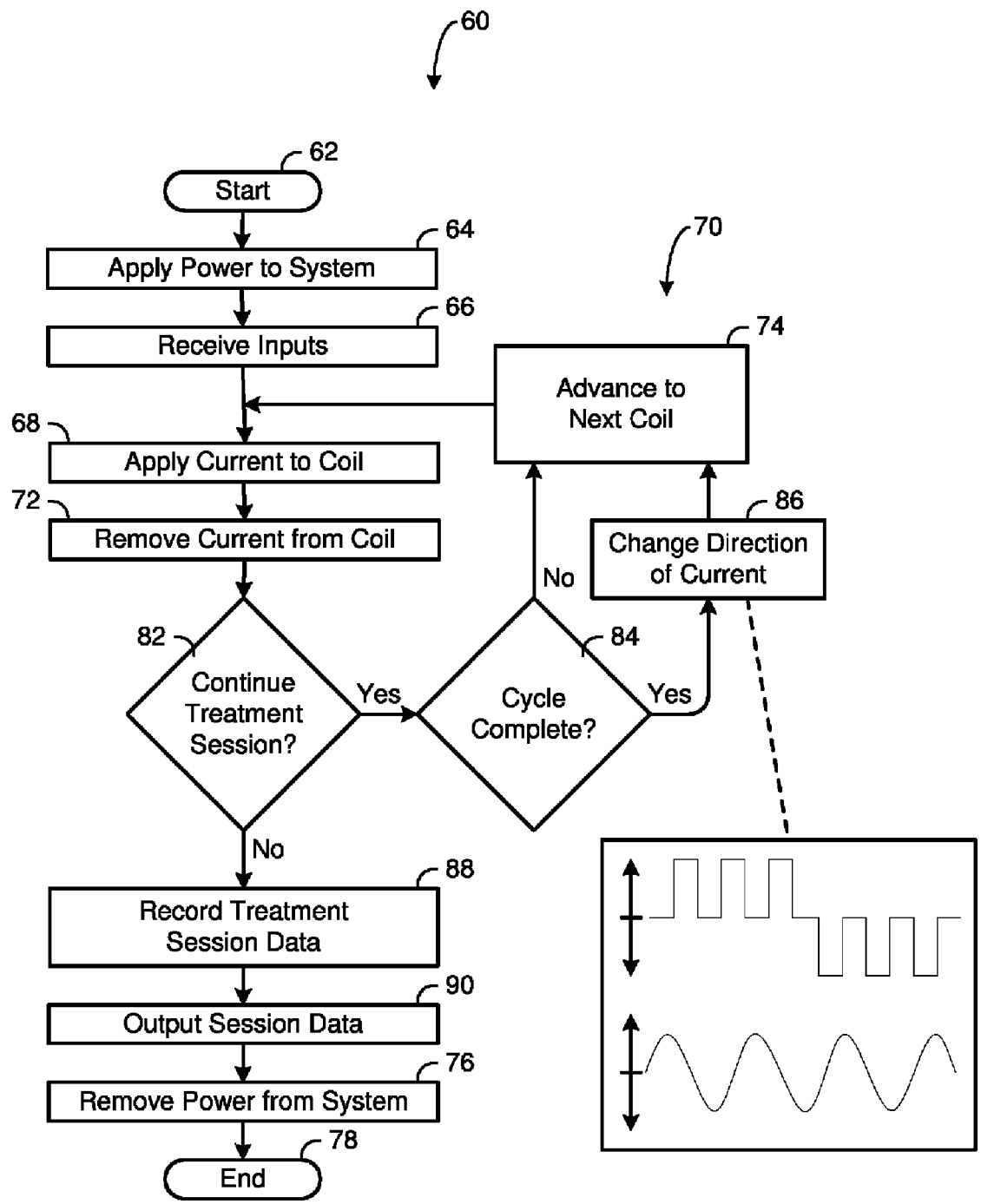
FIG. 7 is a schematic block diagram of a method in accordance with the invention for controlling treatment and recording therapy session data.

Referring to FIG. 7, an alternative method 60 in accordance with the invention may include additional optional steps with respect to the basic process 60 of FIG. 5. For example, after application 64 of power to the system 10, receipt 66 of inputs thereto, application 68 of current to a coil 20, and removal 72 thereof, the return 70 may include additional steps. A decision 82 may be made as to whether continued treatment is to be implemented. This may be accomplished in any suitable manner.

For example, in one embodiment, a controller 14 may include a timer establishing a therapy duration. The controller 14 may enforce that duration by any mechanical, electrical, or electromechanical timer that will shut off current to the coils 20 after a specified duration. For example, a time period from about half an hour to about three hours may be an adequate duration. Times up to ten hours may be effective. Nevertheless, for the use in stabilizing or reversing osteoporosis, between one and a half and two and a half hours may be a suitable duration.

Thus, at the end of a predetermined duration or by any other suitable parameter, the decision 82 may be made to continue or discontinue the present treatment session. If treatment is to be continued, an affirmative answer may result in advancement 74 to the next coil 20. Alternatively, an affirmative answer may lead to an additional decision 84 as to whether a cycle of all the coils 20 within a distributor 12 has been completed. If a cycle of all the coils 20 has not been completed, then an advance 74 may occur, returning to the application 68 of current to the next coil 20 in the sequence. Alternatively, if the cycle has been completed, then a change 86 in the direction of current may be applied.

Certain molecules in the cells of the body are dipoles. They act as small bar magnets rotating to align with a magnetic field 50. Accordingly, it may be beneficial to change 86 the direction of current and thus reverse the polarity of the magnetic field 50 induced by the various coils 20. A change 86 in the direction of the current applied to a coil 20 may be done on every alternate cycle, or after a number of cycles. For example, the direction of current may be changed with each cycle, or with every five cycles, every ten cycles, etc. as determined to be most beneficial. Alternatively, each application 68 of current to a coil 20 may include application of current in both directions (e.g., one followed by the other).

For example, current may be applied 68 at a step function 85, "on" followed by "off" followed by "on." The direction of the current may then be changed 86 and the step function 85 may continue. Alternatively, the current may be applied 68 in an alternating manner (e.g., in a sinusoidal pattern 87) where the current transitions from a maximum peak in one direction to zero to a maximum peak in the opposite direction. When the current is applied 68 in such an alternating manner, there may be no need to determine 84 whether a cycle has been completed, and the process 60 may simply advance 74 to the next coil 20.

When the decision 82 of whether a treatment session should be continued is answered in the negative, application 68 of current to the coils 20 may cease. If desired, certain data characterizing the treatment session may be recorded 88, output 90, or both. In one embodiment, recording 88 the treatment session data may include recording user identification, session duration, current or magnetic field strength, waveform characteristics, or the like.

Such data may assist in determining effectiveness of treatment and monitoring whether the prescribed treatment has been completed. Output 90 of session data may be provided to a centralized computer, printed, or simply displayed so that it may be logged by user patient. Accordingly, information characterizing a treatment session may be used for more general parametric evaluation of the efficacy of treatments over a broad population of patients. Finally, removal 76 of power from the system 10 or disconnection 76 of power from the system 10 results in an end 78 of the treatment.

Figure 8:
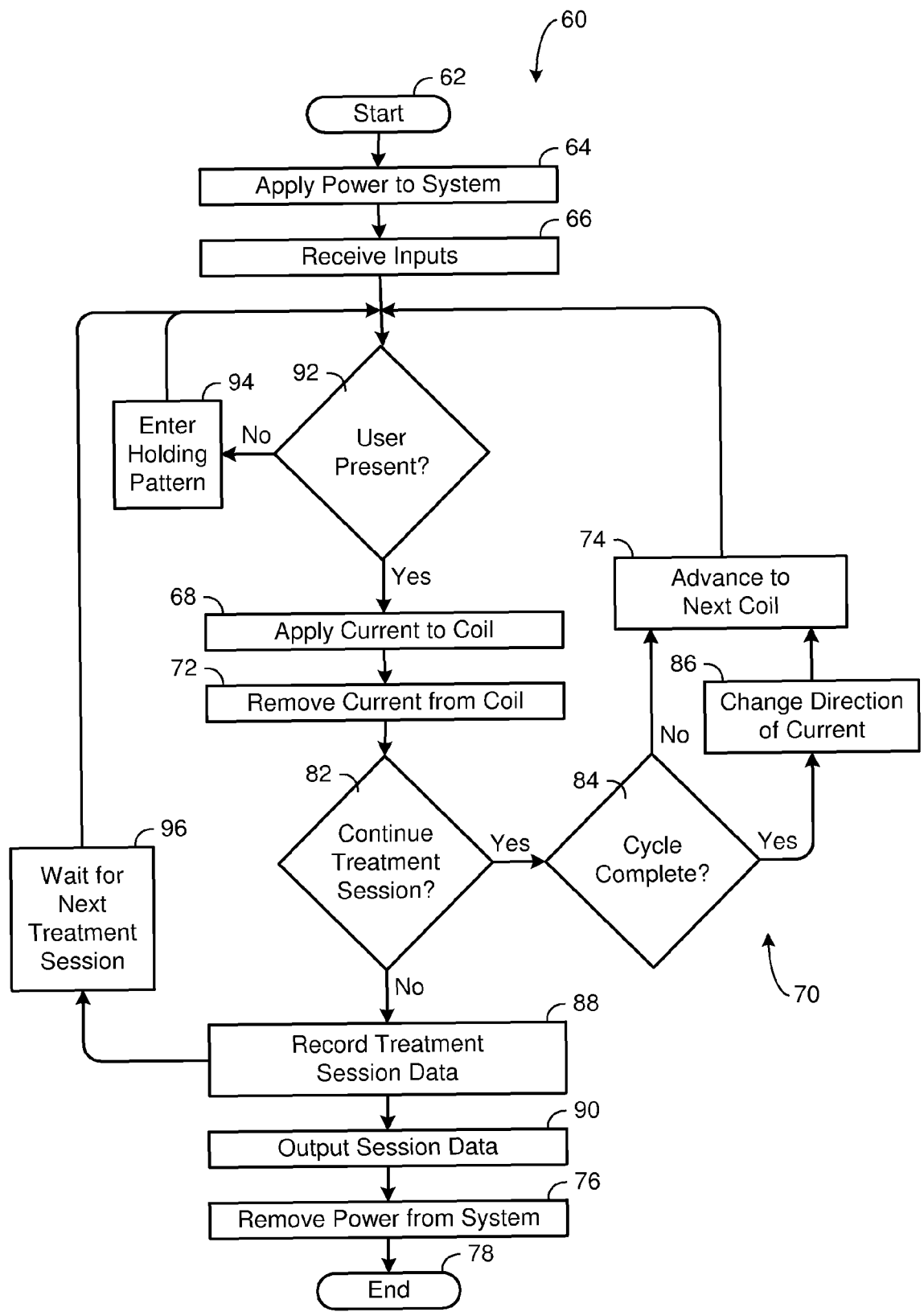
FIG. 8 is a schematic block diagram of a more sophisticated process in accordance with the invention identifying various decisions and options as well as the effect of sensing as a means to control operation of an apparatus in accordance with the present invention.

Referring to FIG. 8, in various applications of medical treatments or other therapies, patient compliance is often a concern. Patient compliance may be limited due to memory issues, confusion, fatigue, or the like. Thus, everything from aptitude to attitude may affect the efficacy or the administration of any treatment.

Accordingly, a method 60 in accordance with the invention may provide for certain user-system interactivity that may aid in compliance. For example, in selected embodiments, a process 60 may include detecting 92 whether a user is present. This may be accomplished by implementation of a sensor of any several types. In one embodiment, a distributor 12 may be installed on a bed as a mattress or mattress cover.

The distributor 12 may include one or more sensors using capacitance, contact, inductance, or the like to detect the presence of a user. A simple pressure contact or capacitance change sensor may detect 92 the presence of a user lying on the bed. When that presence is detected 92, the apparatus 10 may proceed to apply current to the coils 20.

By contrast, if a user is not detected 92, the apparatus 10 may enter 94 a holding pattern and wait unit a user is present (e.g., enter 94 a pattern of periodically polling one or more sensors to determine whether a user is present).

In some embodiments, a controller 14 may utilize an algorithm to determine 92 whether a user is present in a manner suitable for treatment. For example, a user sitting on a bed to put on a pair of shoes, may not be suited for treatment. Accordingly, in selected embodiments, both a particular time of day or night or a particular duration of presence may be required to move on within the process 60. Likewise, if a user is seated, it may be that only sensors near one or two coils may be activated. Accordingly, the controller 14 may determine 92 that the user is not present for treatment. Thus, an algorithm may assist in interpreting the various parameter indicating that a user is present, leading to a better decision 92 as to whether treatment should begin or continue.

In selected embodiments, once the decision 82 has been made to end a treatment session, a system 10 may wait 96 for the next treatment session to begin. The duration of that waiting period 96 may depend upon one or more factors. For example, if a system 10 is dedicated to a particular user (e.g., positioned on the bed of a particular user), the wait 96 may be preprogrammed by a delay time, time of day, or the like.

For example, a typical user will may undergo a period of therapy perhaps once every evening (or every other evening) shortly after retiring. Accordingly, the wait 96 may begin with the end of one treatment session and end the evening of a later day. At that time, the sensors may be activated, permitting the system 10 to again apply 68 current when it is determined 92 that a user is present.

Figure 9:
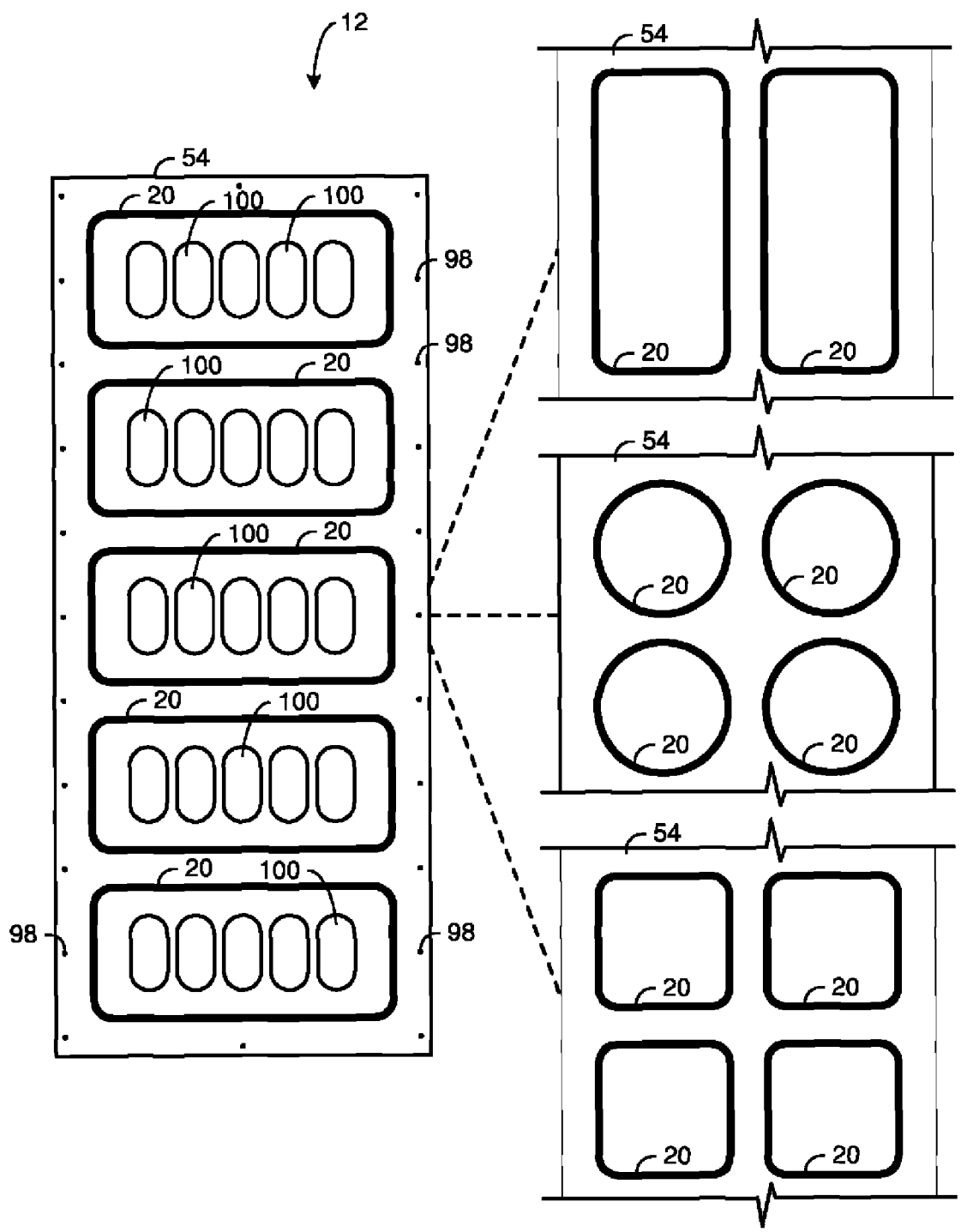
FIG. 9 is a diagram of top plan view of a sensor-equipped distributor with coils of various alternative configurations.

Referring to FIG. 9, a distributor 12 may include one or more user feedback devices 24. In certain embodiments, user feedback devices 24 may be embodied as one or more light emitting diodes 98 (LEDs) arranged on a distributor 12. The LEDs 98 may be configured in any suitable arrangement and be illuminated in any suitable degree, pattern, sequence, or the like.

For example, in one embodiments, LEDs 98 may be positioned along the borders of a distributor 12. The LEDs 98 may be illuminated by a controller 14 whenever current is being applied 68 to the coils 20. Alternatively, certain LEDs 98 may be illuminated whenever to the overall system 10 is powered, while other may be illuminated whenever current is being applied 68 to the coils 20. In one embodiment, LEDs 98 may illuminate only when the coil 20 most proximate thereto is receiving current.

In selected embodiments, a distributor 12 may include one or more sensors 100 distributed throughout the matrix 54. In certain embodiments, the sensors 100 may all be identical. In other embodiments, an array of sensors 100 may include various sensors for different parameters. For example, in selected embodiments, one or more sensors 100 may represent a capacitance detector for pressure. Accordingly, if a user is present, then pressure on one side of a flexible capacitive sensor 100 may decrease capacitance and thereby indicate the presence of a user.

In other embodiments, one or more sensors 100 may be simple contact sensors that indicate pressure as a digital "yes" or "no" ("on" or "off") condition. In still other embodiments, one or more sensors 100 may sense temperature, heart rate, inductance, or the like to detect, monitor, or otherwise provide information to the controller 14. In more sophisticated systems, a pulse, represented by either a repetitive motion or cyclical pressure, or a temperature increase due to the presence of a living person may serve to trigger a sensor 100 to activate the apparatus 10.

Meanwhile, the insets illustrate alternative embodiments of the coils 20 in accordance with the invention. For example, the orientation of the coils 20 may be with their long direction extending in the longitudinal direction of the distributor 12. Likewise, in certain embodiments, the coils 20 may be circular. In other embodiments, the coils 20 may have an aspect ratio closer to one. That is, in certain embodiments, the ratio of width 34 to the length 36 of a coil 20 may approximate a value of unity. In other embodiments, the ratio of the width 34 to the length 36 of a coil 20 may be significantly less then one.

Figure 10:
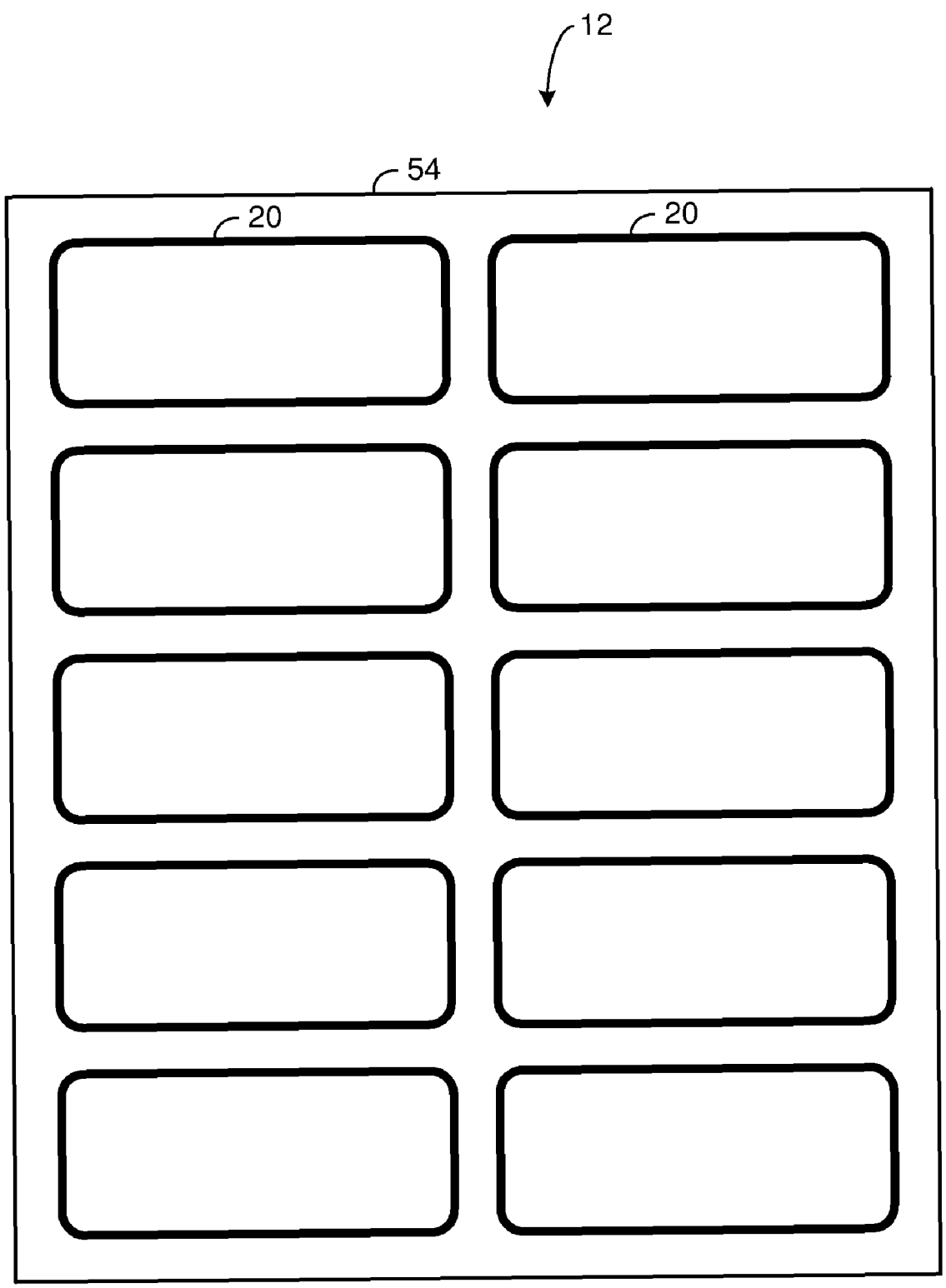

Referring to FIG. 10, an apparatus 10 in accordance with the invention may include a distributor 12 sized to fit a double bed (i.e., double, queen, king, etc.). The matrix 54 may be provided with coils 20 distributed to be separately controllable between two individuals. Accordingly, one array may be aligned with one side of a double bed, whereas another array of coils may be aligned with the other side of the same double bed.

In a simplified embodiment, both sides may be controlled at the same time. Nevertheless, the embodiment of FIG. 10 illustrates one reason why individual controls such as those illustrated in FIGS. 7-8 may efficaciously apply the electromagnetic therapy only when a user is present.

In one embodiment, an apparatus as illustrated in FIGS. 1-4 was configured with the matrix being a blanket containing five coils. The interior width of each coil had a value of 18 cm and the interior length had a value of 48 cm. Each coil included ten turns. The field strength at 30 cm from the blanket surface, was controllable or presetable at from about zero to about 100 micro Tesla (uT), for an effective range of from about 1 to about 100 micro Tesla. The duty cycle target was in the range of from about 5% to about 15%, depending on current flow, with a target of about 7%.

Coils may be connected in series, so long as the direction of current is the same in each, avoiding cancellation. Series connection, or individually activated in sequence, they provided relatively uniform coverage over the dimensions of a whole body covered by the blanket. Field cancellation was largely avoided. In one embodiment, additional coils were added around the periphery of the entire array of the five coils. The overall effect of the peripheral current in the peripheral coil was about one fifth the field strength of the regular coils 20 at 30 cm from the blanket.

Thus, even a simple series connection of the coils can provide a good coverage of the whole volume of the body with the difference between minimum and maximum exposure generally varying by less that about one third.

Typically from about five to about twenty turns make a suitable coil, with ten to twelve turns forming a good design target. However, it was found that the turns per coil can realistically be varied from about one to about 100 or even more with proper engineering. The magnetic field produced is directly proportional to the product of current and number of turns, a small number of turns requires a high current, which requires heavy duty circuitry and robust connectors, but a large number of turns has a high resistance and so requires a high voltage and good quality insulation.

From about 15 to about 60 volts may be preferable for safety, but many countries use 240 volts, while the U.S. uses 115 volts (often characterized as 110 or 120 volt outlet power). For not more than 50 volts, a good compromise is around 10 turns per coil.

With respect to coil dimensions, the field of a circular coil of diameter D at a distance D normal (perpendicular) to the plane of the coil, the field strength is about 45% of the field at the center of the coil in the plane of the coil. With rectangular coils 60 cm×30 cm, the field strength 30 cm from the center of the coil along its axis of symmetry is slightly above 50% of the field at the center of the coil. Thus dimensions of 60 cm×30 cm are adequate for good field penetration and even distribution to a depth of at least about 40 cm. Coils 50 cm×25 cm are adequate but might be regarded as the smaller end of the size range effective for full body exposure. However, they require proportionately less current for the same field strength exposure.

In one engineered design, a single peripheral coil of from about 15 to about 40 turns, having a (maximum) pulsed current from about 10 to about 15 amperes provides about the same weight of conductor as a five-coil distributor. Fabrication is simpler, cheaper and field exposure is more uniform. However, user perception has a psychological effect. A user may think (incorrectly) that the absence of coils in the main area of the blanket is a disadvantage.

High frequencies such as radio frequency (RF) waves produce heating but no known, physio-chemical response in mammalian tissue. However, an apparatus and method in accordance with the invention induces currents in circuits within its fields. Likewise, those currents distribute voltages across all elements of tissue circuits that conduct. Accordingly, all circuits that include bone cells as elements expose that piezoelectric bone to a potential, e.g. voltage, inducing a stress (load force per unit area) and a strain (displacement length per unit length), prompting a response by the organism. The stress, strain, and potential appear to be consistent with exercise, and the physiology of the organism (e.g. person, animal) may respond as if it were. Thus, frequencies of from about 1 Hertz (i.e. low values, single digits or fractions) up to about 100 Hertz may trigger or otherwise couple with such physiological responses.

In addition, a mammalian body has immune and nervous systems having chemical reactions that generate electrical signals. These may respond repetitively at a communication frequency of from about 10 to about 100 Hertz. On the other hand, a single response may often be triggered by pulses of much shorter duration. Thus, a repetition rate in the range of from about 10 Hertz to about 1000 Hertz may rely on comparatively shorter pulses.

A duty cycle in the range of 2 to 15% with the above pulse repetition rates may cause a repetitive electrochemical stimulation in the body simulating use of parts by communicating as much, even without actually loading these tissues.

For stimulation effect caused by induced potential, the pulse shape may be sharp, i.e. a square or rectangular pulse waveform, or a comparatively short duration sinusoidal waveform at frequencies corresponding to bodily electrical functions. A very much slower rise is not contemplated to be effective for this type of coupling.

A repetition rate of from about 100 Hertz to about 300 Hertz provides a frequency similar to that of the immune system, relevant body mechanisms, or both, in vigorous exercise. It is contemplated that a duration of from about one half hour to about 2 hours per day. A repetition frequency of 3 to 5 sessions (days of treatment) per week is consistent with exercise rates known to be effective in maintaining general health.

In one embodiment, a magnetic field of up to 100 uT may be supplied to the bulk of a human body at a pulse repetition rate of from about 50 to about 500 Hz. A duty cycle of over 1% and preferably from about 5% to about 15% may ensure a magnetic pulse long enough for the body electrochemical processes to be stimulated. A rectangular or rapidly rising and falling current pulse shape or waveform from a large, single magnetic coil having from about 5 to about 50 turns extending around a blanket, proximate the perimeter thereof may serve well. Sequencing current delivery to an array of from 1 to about 6 coils, each having from about 5 to about 15 coils, and preferably about 10 turns each may cover the same area.

A treatment period may operate with power inputs greater than 1 VA, and typically may draw from about 5 to about 10 VA of power. During each cycle, the pulses may be reversed in a manner to provide about an equal number of magnetic pulses in the forward and reverse directions. For this and other reason there need be no requirement for any specific orientation of the blanket.

The frequency and field range provided by the coils of a distributor, such as one with a blanket or mattress pad acting as a matrix, may be fixed or adjustable by a user or caretaker.

It may also be regularly cycled, or timed by calendar or computer clock as to repetition of sessions, or the like.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A method of increasing bone mass throughout the body of a user, the method comprising:
    obtaining a distributor comprising a blanket containing a plurality of coils, each coil configured to conduct electrical current and generate an electromagnetic field in response thereto;
    obtaining a controller comprising a processor and a memory device, operably connected to one another, the memory device storing code executable by the processor;
    selecting a source of electrical current;
    connecting the source to the controller;
    retiring, by a user, to a nightly bed of the user to sleep for a night;
    positioning the blanket over the user in the nightly bed;
    delivering, after the retiring and positioning, electrical current to the plurality of coils, and
    controlling, by the controller in accordance with the code, the delivering of electrical current sequentially and exclusively to each coil of the plurality of coils to generate an electro magnetic field extending therethrough and into the user.

2. The method of claim 1, wherein the plurality of coils are positioned adjacent one another in a non-overlapping arrangement.

3. The method of claim 2, wherein each coil of the plurality of coils is positioned to be substantially coplanar.

4. The method of claim 3, wherein the distributor further comprises a matrix comprising a flexible, breathable, material covering and mechanically connecting the plurality of coils.

5. The method of claim 4, further comprising positioning the distributor coextensively over an upper surface of a bed sized to accommodate the user during sleep.

6. The method of claim 5, further comprising triggering operation of the distributor in accordance with the presence of a user weighting the upper surface of the bed.

7. The method of claim 6, further comprising distributing, intermittently, by the controller, the current among to the coils for a duration of from about a quarter hour to about four hours with, a duty cycle of actual current duration from about 1 percent to about 15 percent.

8. The method of claim 1, wherein the controller further comprises a sensor operably connected to provide inputs to the processor indicating the presence of a user proximate the plurality of coils, the method further comprising:
    sensing by the sensor a separation of a user from the distributor;
    ceasing by the controller the delivering of current to the plurality of coils, in accordance with a first input from the sensor reflecting the separation; and
    resumption of the delivering of current in response to a second input from the sensor reflecting a subsequent closure of the separation.

9. The method of claim 1, wherein the controller further comprises a sensor associated with the distributor to detect the presence of a user, the method further comprising distributing by the controller the current to the coils only during a period of time during which the sensor detects the presence of a user.

10. A method of treatment to increase bone density in a mammalian subject, the method comprising:
    selecting a distributor comprising a blanket containing at least one coil set in a matrix, the at least one coil configured to conduct electrical current and generate an electromagnetic field in response thereto;
    selecting a controller comprising a processor and a memory device, operably connected to one another, the memory device storing code executable by the processor to control delivery of the electrical current to the at least one coil;
    connecting the controller to a source of electrical current;
    retiring, by a user, to a nightly bed of the user to sleep for a night;
    positioning the blanket over the user in the nightly bed;
    delivering, after the retiring and positioning, electrical current sequentially to each of the at least one coil to generate a magnetic field extending therethrough and substantially through the subject.

11. The method of claim 10, wherein:
    the at least one coil comprises a plurality of coils positioned adjacent one another in a non-overlapping arrangement; and
    the coils of the plurality of coils are positioned to be substantially coplanar.

12. The method of claim 10, wherein the matrix comprises a flexible, breathable, material covering and mechanically connecting the at least one coil.

13. The method of claim 10, further comprising:
    positioning the distributor coextensively over an upper surface of a bed sized to accommodate the subject during sleep;
    sensing by a sensor the presence of the subject on the bed;
    inputting to the controller an input from the sensor reflecting the presence; and
    controlling by the controller operation of the distributor in accordance with the input.

14. The method of claim 10, further comprising:
    providing a sensor delivering inputs to the processor indicating the presence of a subject proximate the at least one coil;
    ceasing, by the controller, the delivering of current to the at least one coil, in accordance with a first input from the sensor reflecting separation of the subject from the at least one coil; and
    resuming, by the controller, the delivering of current in response to a second input from the sensor reflecting a subsequent closure of the separation.

\* \* \* \* \*